US008623007B2

(12) United States Patent
Deborski et al.

(10) Patent No.: US 8,623,007 B2
(45) Date of Patent: Jan. 7, 2014

(54) ELECTROSURGICAL GENERATOR TO ABLATION DEVICE ADAPTOR

(75) Inventors: Christopher A. Deborski, Denver, CO (US); Anthony B. Ross, Boulder, CO (US); Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 788 days.

(21) Appl. No.: 12/826,879

(22) Filed: Jun. 30, 2010

(65) Prior Publication Data

US 2012/0004703 A1  Jan. 5, 2012

(51) Int. Cl.
*A61B 18/14* (2006.01)
(52) U.S. Cl.
USPC .............................. 606/34; 606/32
(58) Field of Classification Search
USPC ................. 606/32–35, 41, 42, 45–50
See application file for complete search history.

(56) References Cited

U.S. PATENT DOCUMENTS

| | | | |
|---|---|---|---|
| 3,952,748 | A | 4/1976 | Kaliher et al. |
| 4,200,105 | A * | 4/1980 | Gonser ........................... 606/35 |
| 5,318,563 | A | 6/1994 | Malis et al. |
| 5,954,686 | A | 9/1999 | Garito et al. |
| 6,113,596 | A * | 9/2000 | Hooven et al. .................. 606/42 |
| 6,652,514 | B2 | 11/2003 | Ellman et al. |
| 7,094,231 | B1 | 8/2006 | Ellman et al. |
| D574,323 | S | 8/2008 | Waaler |
| 7,909,820 | B2 * | 3/2011 | Lipson et al. ................... 606/34 |
| 2004/0030330 | A1 | 2/2004 | Brassell et al. |

FOREIGN PATENT DOCUMENTS

| | | |
|---|---|---|
| DE | 179607 | 3/1905 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |

(Continued)

OTHER PUBLICATIONS

Wald et al., "Accidental Burns", JAMA, Aug. 16, 1971, vol. 217, No. 7, pp. 916-921.

(Continued)

*Primary Examiner* — Michael Peffley

(57) ABSTRACT

An electrosurgical system is provided that includes an electrosurgical generator configured to output a first electrosurgical waveform and a probe configured to deliver a second electrosurgical waveform to tissue. The system also includes an adapter coupled between the electrosurgical generator and the probe and operable to convert the first electrosurgical waveform to the second electrosurgical waveform. The adapter includes a step down transformer configured to convert the first electrosurgical waveform to the second electrosurgical waveform.

13 Claims, 3 Drawing Sheets

(56) References Cited

FOREIGN PATENT DOCUMENTS

| | | |
|---|---|---|
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |

OTHER PUBLICATIONS

Vallfors et al., "Automatically Controlled Bipolar Electrosoagulation-'COA-COMF'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. Ml, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight And Absorbance Imaging Of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.

(56) References Cited

OTHER PUBLICATIONS

International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

* cited by examiner

ELECTROSURGICAL GENERATOR TO ABLATION DEVICE ADAPTOR

BACKGROUND

1. Technical Field

The present disclosure relates generally to electrosurgical systems that utilize energy to perform electrosurgical procedures. More particularly, the present disclosure is directed to an adaptor capable of connecting an ablation device to an electrosurgical generator to perform ablations.

2. Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such ablation procedures, e.g., such as those performed for menorrhagia, are typically done to ablate and coagulate the targeted tissue to denature or kill the tissue. Many procedures and types of devices utilizing electromagnetic radiation therapy are known in the art. Such therapy is typically used in the treatment of tissue and organs such as the prostate, heart, liver, lung, kidney, and breast.

One non-invasive procedure generally involves the treatment of tissue (e.g., a tumor) underlying the skin via the use of radio frequency (RF) energy. The RF energy is able to non-invasively penetrate the skin to reach the underlying tissue. However, this non-invasive procedure may result in the unwanted heating of healthy tissue. Thus, the non-invasive use of RF energy requires a great deal of control.

RF ablation devices utilize the same or similar frequencies as electrosurgical devices. Accordingly, an electrosurgical generator should be able to drive an RF ablation device. However, there are challenges when trying to perform an RF ablation procedure using an electrosurgical device. For instance, although RF ablation devices and electrosurgical devices utilize similar frequencies, the different devices utilize different voltage and current waveforms. Electrosurgical devices utilize high voltage low current waveforms while RF ablation devices utilize high current low voltage waveforms.

Further, the connectors available with current RF ablation devices and electrosurgical generators are not complimentary. As such, RF ablation devices in existence can not be coupled to available electrosurgical devices.

SUMMARY

The present disclosure relates to an electrosurgical system that includes an electrosurgical generator configured to output a first electrosurgical waveform and a probe configured to deliver a second electrosurgical waveform to tissue. The system also includes an adapter coupled between the electrosurgical generator and the probe and operable to convert the first electrosurgical waveform to the second electrosurgical waveform. The adapter includes a step down transformer configured to convert the first electrosurgical waveform to the second electrosurgical waveform.

In one embodiment, the first electrosurgical waveform has a higher voltage level than the second electrosurgical waveform. Moreover, the first electrosurgical waveform has a lower current level than the second electrosurgical waveform.

In another embodiment, the system also includes a return electrode configured to receive a third electrosurgical waveform from tissue. The return electrode is coupled to the adapter and configured to deliver the received third electrosurgical waveform to the adapter, wherein the adapter includes a step up transformers operable to convert the third electrosurgical waveform received by the return electrode to a fourth electrosurgical waveform. The fourth electrosurgical waveform has a higher voltage level than the third electrosurgical waveform and a lower current level than the third electrosurgical waveform.

In yet another embodiment, an adapter suitable to connect a radio frequency ablation probe and return electrode to an electrosurgical generator is provided. The adapter includes a first transformer configured to receive a first electrosurgical waveform from the electrosurgical generator and convert the first electrosurgical waveform to a second electrosurgical waveform that is delivered to the radio frequency ablation probe. The adapter also includes a second transformer configured to convert a third electrosurgical waveform from the return electrode to a fourth electrosurgical waveform that is delivered to the electrosurgical generator.

The first electrosurgical waveform has a higher voltage level than the second electrosurgical waveform and a lower current level than the second electrosurgical waveform. Moreover, the fourth electrosurgical waveform has a higher voltage level than the third electrosurgical waveform and a lower current level than the third electrosurgical waveform.

In yet another embodiment, the adapter may also include a sensor module configured to detect at least one parameter of the first electrosurgical waveform, the second electrosurgical waveform, the third electrosurgical waveform or the fourth electrosurgical waveform where the parameter is a voltage magnitude and/or phase or current magnitude and/or phase. Additionally, the adapter may also include a controller operable to control the first transformer or the second transformer.

BRIEF DESCRIPTION OF THE DRAWINGS

Objects and features of the presently disclosed systems and methods will become apparent to those of ordinary skill in the art when descriptions of various embodiments thereof are read with reference to the accompanying drawings, of which.

DETAILED DESCRIPTION

Figure 1:
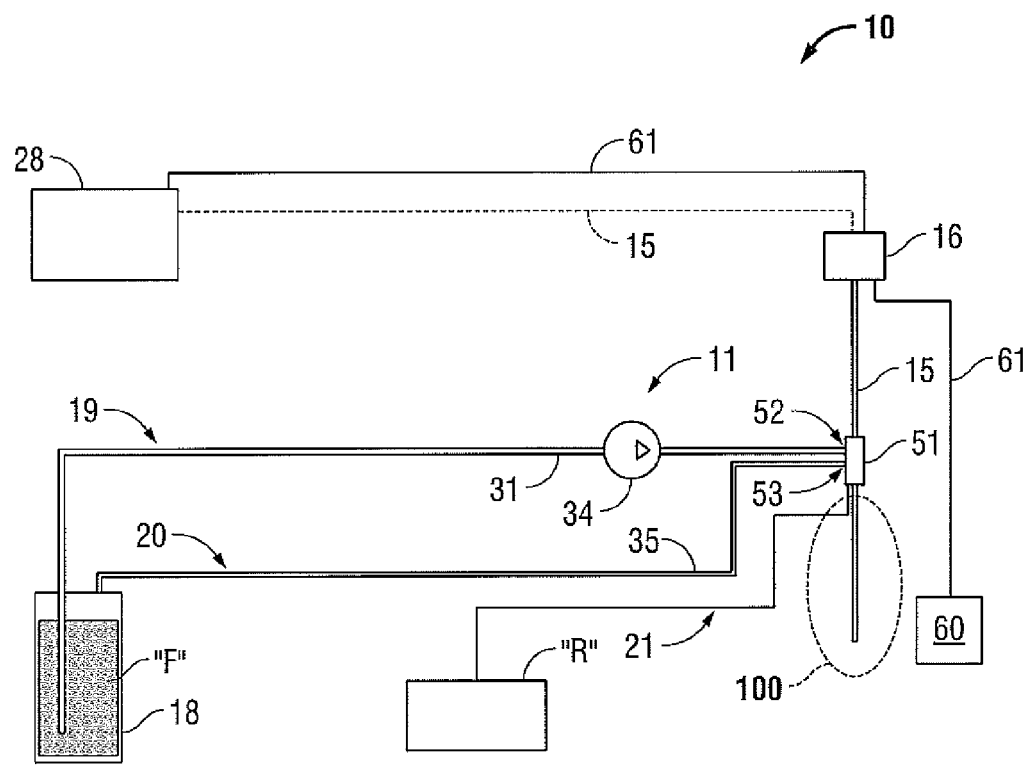
FIG. 1 is a schematic diagram of an electrosurgical system including a coolant supply system according to an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Electromagnetic energy is generally classified by increasing energy or decreasing wavelength into radio waves, microwaves, infrared, visible light, ultraviolet, X-rays and gamma-rays. As used herein, the term "RF" generally refers to electromagnetic waves in the frequency range of 1 MHz or lower. The phrase "transmission line" generally refers to any transmission medium that can be used for the propagation of signals from one point to another.

Various embodiments of the presently disclosed electrosurgical systems including an energy applicator in fluid communication with a coolant supply system are suitable for RF ablation and for use to pre-coagulate tissue for RF ablation assisted surgical resection. Although various methods described hereinbelow are targeted toward RF ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue.

FIG. 1 shows an electrosurgical system 10 according to an embodiment of the present disclosure that includes an electrode probe 100. An embodiment of electrode probe 100 of FIG. 1, in accordance with the present disclosure, is shown in more detail in FIG. 2. It will be understood, however, that other electrode probe embodiments may also be used.

Electrosurgical system 10 includes a return electrode 60 connected to adapter 16 via transmission line 61 which may further be operatively connected to electrosurgical generator 28. Energy outputted by probe 100 is received by return electrode 60 and provided as a feedback to electrosurgical generator 28 which is used to directly or indirectly control electrosurgical generator 28. The return electrode 60 may have any suitable regular or irregular shape such as circular or polygonal. Return electrode 60 may be a conductive pad that may include a plurality of conductive elements arranged in a regular or irregular array. Each of the plurality of conductive elements may be equally-sized or differently-sized and may form a grid/array on the conductive pad. The plurality of conductive elements may also be arranged in a suitable spiral or radial orientation on the conductive pad. The use of the term "conductive pad" as described herein is not meant to be limiting and may indicate a variety of different pads including, but not limited to, conductive, inductive, or capacitive pads.

Electrosurgical system 10 in accordance with an embodiment of the present disclosure includes an electrosurgical generator 28 and a coolant supply system 11 adapted to provide coolant fluid "F" to the probe 100. In some embodiments, the coolant supply system 11 includes a coolant source 18, and may include a substantially closed loop having a first coolant path 19 leading to the probe 100 and a second coolant path 20 leading from the probe 100. The size and shape of the first coolant path 19 and the second coolant path 20 may be varied from the configuration depicted in FIG. 1. In other embodiments, the coolant supply may have an open loop configuration as shown in FIG. 1 where coolant follows a third coolant path 21 to a reservoir "R" so that coolant is not recirculated.

Hub 51 may be in fluid communication with the coolant source 18 via the first coolant path 19 and/or the second coolant path 20. In some embodiments, the coolant supply system 11 includes a first coolant path 19 and a second coolant path 20, wherein the first coolant path 19 includes a coolant supply line 31 leading from the coolant source 18 to a coolant inlet port 52 that is defined in the hub 51, and the second coolant path 20 includes a coolant return line 35 leading from a coolant outlet port 53 that is defined in the hub 51 to the coolant source 18.

Coolant source 18 may be any suitable housing containing a reservoir of coolant fluid "F". Coolant fluid "F" may be any suitable fluid that can be used for cooling the probe 100, e.g., water, or other suitable cooling medium. Coolant fluid "F" may be a conductive fluid, such as a saline solution, which may be delivered to the target tissue, e.g., to decrease impedance and allow increased power to be delivered to the target tissue. A coolant fluid "F" composition may vary depending upon desired cooling rates and the desired tissue impedance matching properties. Various fluids may be used, e.g., liquids including, but not limited to, water, saline, perfluorocarbon, such as the commercially available Fluorinert® perfluorocarbon liquid offered by Minnesota Mining and Manufacturing Company (3M), liquid chlorodifluoromethane, etc. In other variations, gases (such as nitrous oxide, nitrogen, carbon dioxide, etc.) may also be utilized as the cooling fluid. In yet another variation, a combination of liquids and/or gases, including, for example, those mentioned above, may be utilized as the coolant fluid "F".

As shown in FIG. 1, a fluid movement device 34 may be provided in the first coolant path 19 to move the coolant fluid "F" through the first coolant path 19. Fluid movement device 34 may include valves, pumps, power units, actuators, fittings, manifolds, etc. The position of the fluid movement device 34 may be varied from the configuration depicted in FIG. 1. Fluid movement device 34 may additionally, or alternatively, be provided in the second coolant path 20. Although the coolant supply system 11 shown in FIG. 1 includes a single, fluid movement device 34 positioned in the first coolant path 19, various combinations of different numbers of fluid movement devices, variedly sized and variedly spaced apart from each other, may be provided in the first coolant path 19, the second coolant path 20, and/or the third coolant path 21.

Electrosurgical generator 28 may be configured to provide various frequencies of electromagnetic energy. Transmission line 15 may additionally, or alternatively, provide a conduit (not shown) configured to provide coolant fluid "F" from the coolant source 18 to the probe 100.

Figure 2:
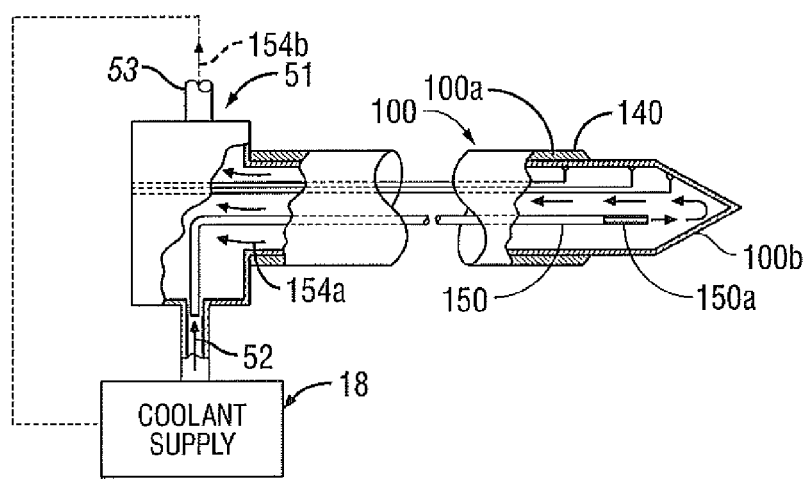
FIG. 2 is a broken-away partial cross-section view of a tip of an electrode probe shown in FIG. 1 according to an embodiment of the present disclosure.

As shown in FIG. 2, each electrode probe 100 includes a non-exposed proximal rigid shaft 100a that is surrounded by an insulating material 140, and a non-insulated distal tip 100b exposed for DC or AC, preferably RF delivery. At its proximal end, electrode probe 100 is typically integrally associated with a hub 51 that carries electrical and coolant connections to electrode probe 100.

Temperatures at, or near distal tip 100b of electrode probe 100 may be controlled by adjusting a flow of fluid coolant through electrode probe 100. Accordingly, the temperature of the tissue contacting at or near distal tip 100b is controlled. In operation, fluid from a coolant source 18 is carried the length of electrode probe 100 through a tube 150 extending from hub 51 to the distal end of electrode probe 100 terminating in an open end 150a at distal tip 100b. At the opposite end of electrode probe 100, within hub 51, tube 150 is connected to receive fluid. Backflow from distal tip 100*b* is through an coolant outlet port 53 of hub 51 as illustrated by arrows 154*a*, 154*b*.

During ablation, e.g., using the electrosurgical system 10, the probe 100 is inserted into or placed adjacent to tissue and RF energy is supplied thereto. Ultrasound or computed tomography (CT) guidance may be used to accurately guide the probe 100 into the area of tissue to be treated. Probe 100 may be placed percutaneously or atop tissue, e.g., using conventional surgical techniques by surgical staff. A clinician may pre-determine the length of time that energy is to be applied. Application duration may depend on many factors such as tumor size and location and whether the tumor was a secondary or primary cancer. The duration of energy application using the probe 100 may depend on the progress of the heat distribution within the tissue area that is to be destroyed and/or the surrounding tissue. Single or multiple probes 100 may provide ablations in short procedure times, e.g., a few minutes, to destroy cancerous cells in the target tissue region.

Figure 3:
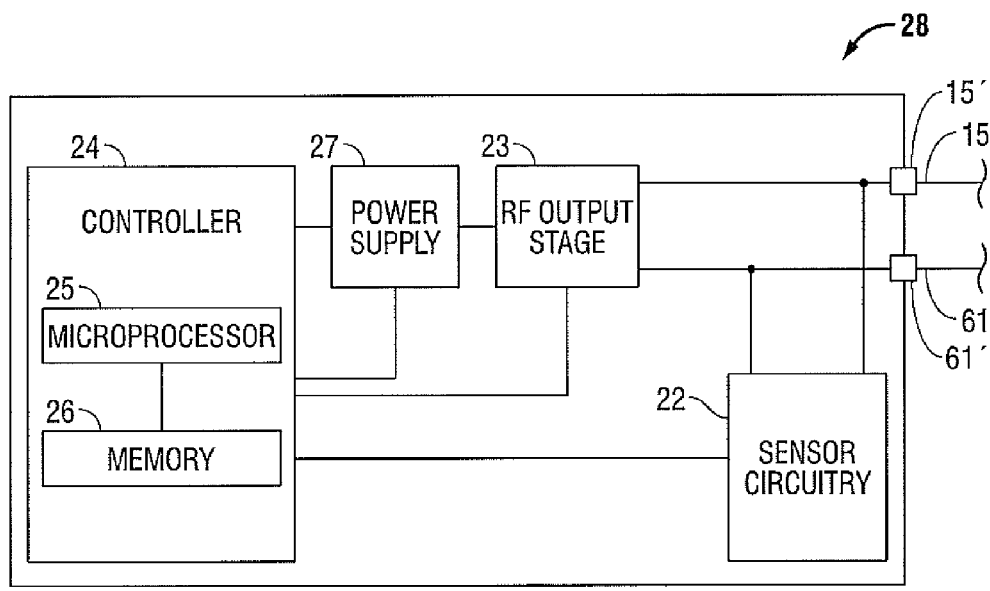
FIG. 3 is a schematic block diagram of a electrosurgical generator according to an embodiment of the present disclosure.

FIG. 3 shows a schematic block diagram of the electrosurgical generator 28 having a controller 24, a power supply 27, an RF output stage 23, and a sensor module 22. The power supply 27 provides DC power to the RF output stage 23 which then converts the DC power into RF energy and delivers the RF energy to the probe 100 via active terminal 15'. The controller 24 includes a microprocessor 25 having a memory 26 which may be volatile type memory (e.g., RAM) and/or non-volatile type memory (e.g., flash media, disk media, etc.). The microprocessor 25 includes an output port connected to the power supply 27 and/or RF output stage 23 that allows the microprocessor 25 to control the output of the electrosurgical generator 28 according to either open and/or closed control loop schemes. RF energy returns to electrosurgical generator 28 via transmission line 61 which is operatively coupled to return terminal 61'.

A closed loop control scheme generally includes a feedback control loop wherein the sensor module 22 provides feedback to the controller 24 (i.e., information obtained from one or more sensing mechanisms for sensing various tissue parameters such as tissue impedance, tissue temperature, output current and/or voltage, etc.). The controller 24 then signals the power supply 27 and/or RF output stage 23 which then adjusts the DC and/or RF power supply, respectively. The controller 24 also receives input signals from the input controls of the electrosurgical generator 28. The controller 24 utilizes the input signals to adjust the power output of the electrosurgical generator 28 and/or instructs the electrosurgical generator 28 to perform other control functions.

The microprocessor 25 is capable of executing software instructions for processing data received by the sensor module 22, and for outputting control signals to the electrosurgical generator 28, accordingly. The software instructions, which are executable by the controller 24, are stored in the memory 26 of the controller 24.

The controller 24 may include analog and/or logic circuitry for processing the sensed values and determining the control signals that are sent to the electrosurgical generator 28, rather than or in combination with, the microprocessor 25.

The sensor module 22 may include a plurality of sensors (not explicitly shown) strategically located for sensing various properties or conditions, e.g., tissue impedance, voltage at the tissue site, current at the tissue site, etc. The sensors are provided with leads (or wireless) for transmitting information to the controller 24. The sensor module 22 may include control circuitry that receives information from multiple sensors, and provides the information and the source of the information (e.g., the particular sensor providing the information) to the controller 24.

More particularly, the sensor module 22 may include a real-time voltage sensing system (not explicitly shown) and a real-time current sensing system (not explicitly shown) for sensing real-time values related to applied voltage and current at the surgical site such as magnitude and/or phase. Additionally, an RMS voltage sensing system (not explicitly shown) and an RMS current sensing system (not explicitly shown) may be included for sensing and deriving RMS values for applied voltage and current at the surgical site.

The electrosurgical generator 28 includes suitable input controls (e.g., buttons, activators, switches, touch screen, etc.) for controlling the electrosurgical generator 28, as well as one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., tissue ablation). Further, the probe 100 may include a plurality of input controls which may be redundant with certain input controls of the electrosurgical generator 28. Placing the input controls at the probe 100 allows for easier and faster modification of RF energy parameters during the surgical procedure without requiring interaction with the electrosurgical generator 28.

A generator according to the present disclosure can perform monopolar and bipolar electrosurgical procedures, including tissue ablation procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 4:
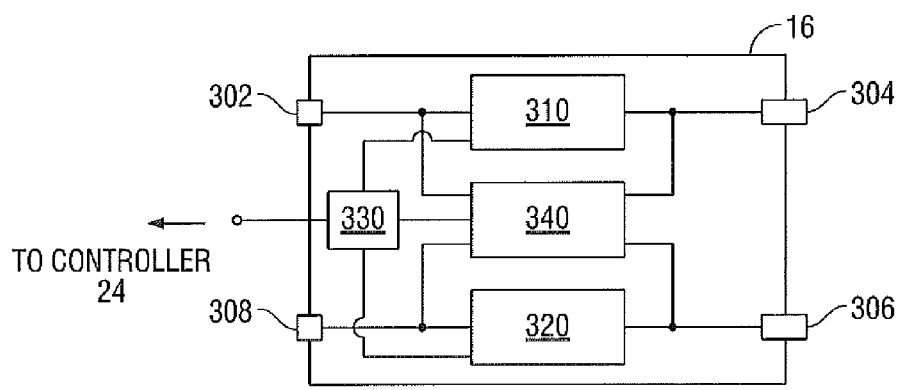
FIG. 4 is a schematic block diagram of an adapter for use in an electrosurgical system according to an embodiment of the present disclosure.

Turning to FIG. 4, a schematic block diagram of an adapter for use in an electrosurgical system is shown generally as 16. Adapter 16 includes an input port 302 that is operatively coupled to active terminal 15' of electrosurgical generator 28 (FIG. 3). RF energy supplied by electrosurgical generator 28 is provided to step down transformer 310. Step down transformer 310 provides an electrosurgical waveform output having a lower voltage and a higher current than the RF energy from electrosurgical generator 28. The output of step down transformer 310 is coupled to output port 304 which is operatively coupled to probe 100. As such, step down transformer 310 provides the converted RF energy to probe 100. By using adapter 16, an electrosurgical generator may be used to provide energy suitable for use with an RF ablation probe. Further, input port 302 includes a connector that is compatible with the electrosurgical generator 28 while output port 304 includes a connector that is compatible with probe 100.

Adapter 16 also includes a step up transformer 320 coupled between a return electrode input port 306 and an output port 308. Input port 306 is operatively coupled to return electrode 60 (FIG. 1). RF energy from return electrode 60 is converted by step up transformer 320 to an electrosurgical waveform, which is compatible with electrosurgical generator 28, having a higher voltage and a lower current than the RF energy from return electrode 60. The converted RF energy is provided to electrosurgical generator 28 via output port 308 that is operatively coupled to return terminal 61' of electrosurgical generator 28 (FIG. 3). Input port 306 includes a connector that is compatible with probe 100 while output port 308 includes a connector that is compatible with electrosurgical generator 28.

The electrosurgical waveform outputted from output port 304 and the electrosurgical waveform inputted into return electrode input port 306 may have a substantially similar frequency.

Adapter 16 may include an optional controller 330. Controller 330 may include analog and/or logic circuitry for processing signals from controller 24 to control transformers 310 and 320. For instance, transformers 310 and 320 may be variable transformers and controller 330 may adjust transformers 330 to achieve a desired output. Alternatively, transformers 310 and 330 may be operatively coupled to controller 28 which may then control the outputs of transformers 310 and 320 directly.

A sensor module 340 may also be provided that includes a real-time voltage sensing system (not explicitly shown) and a real-time current sensing system (not explicitly shown) for sensing real-time values related to applied voltage and current at the surgical site such as magnitude and/or phase. Sensor module 340 may sense input voltage and current or output voltage and current of transformers 310 and 330 and provide the detected values to controller 340 or to controller 24. Alternatively, sensor module 340 may calculate power and/or impedance levels based on the sensed voltage and current levels. The calculated power and/or impedance values may be provided to controller 340 or controller 24 to control the output of the electrosurgical system.

Figure 5:
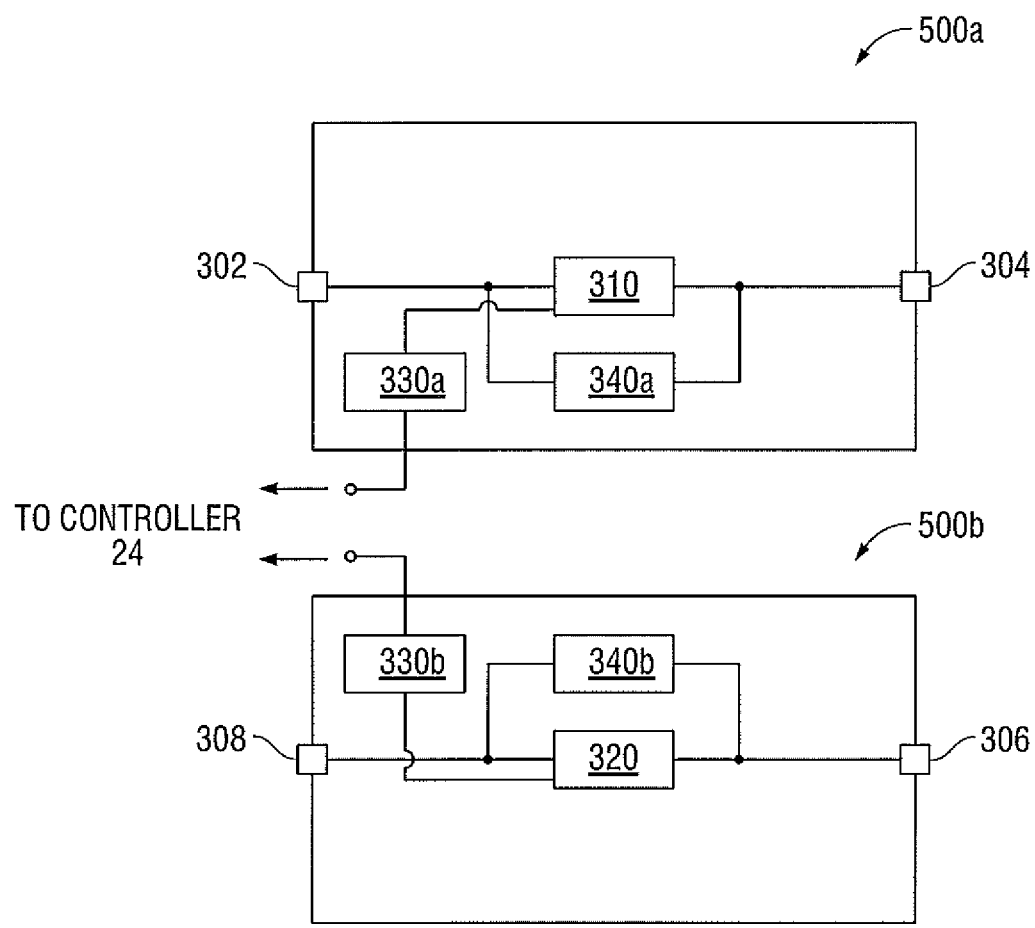
FIG. 5 is a schematic block diagram of a pair of adapter for use in an electrosurgical system according to another embodiment of the present disclosure.

Alternatively, adapter 16 may be provided as a single adapter or two adapters 500a and 500b as shown in FIG. 5. Adapters 500a and 500b include components similar to adapter 16. As such, operation of similar components will not be discussed in great detail.

As shown in FIG. 5, adapter 500a includes an input port 302 that is operatively coupled to active terminal 15' of electrosurgical generator 28 (FIG. 3). RF energy supplied by electrosurgical generator 28 is provided to step down transformer 310. Step down transformer 310 provides an electrosurgical waveform output having a lower voltage and a higher current than the RF energy from electrosurgical generator 28. The output of step down transformer 310 is coupled to output port 304 which is operatively coupled to probe 100. As such, step down transformer 310 provides the converted RF energy to probe 100.

Adapter 500b includes a step up transformer 320 coupled between a return electrode input port 306 and an output port 308. Input port 306 is operatively coupled to return electrode 60 (FIG. 1). RF energy from return electrode 60 is converted by step up transformer 320 to an electrosurgical waveform, which is compatible with electrosurgical generator 28, having a higher voltage and a lower current than the RF energy from return electrode 60. The converted RF energy is provided to electrosurgical generator 28 via output port 308 that is operatively coupled to return terminal 61' of electrosurgical generator 28 (FIG. 3).

Adapter 500a and adapter 500b may each include an optional controller 330a, 330b and a sensor module 340a, 340b as described above with reference to FIG. 4.

Although specific embodiments of the present disclosure have been described above, many alternatives may be contemplated without departing from the scope of the present disclosure. For instance, adapter 16 may be coupled directly to electrosurgical generator 28 or probe 100 without the use of a transmission line. Further, sensor module 22 may be used to senses voltage and/or current at the input and output of the step up or step down transformer.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. The claims can encompass embodiments in hardware, software, or a combination thereof. Those skilled in the art will envision other modifications within the scope and spirit of the claims appended hereto.

What is claimed is:

1. An electrosurgical system, comprising:
an electrosurgical generator configured to output a first electrosurgical waveform; a probe configured to deliver a second electrosurgical waveform to tissue;
an adapter coupled between the electrosurgical generator and the probe and operable to convert the first electrosurgical waveform to the second electrosurgical waveform, the adapter including a step down transformer configured to convert the first electrosurgical waveform to the second electrosurgical waveform;
a return electrode configured to receive a third electrosurgical waveform from tissue, the return electrode being coupled to the adapter and configured to deliver the received third electrosurgical waveform to the adapter, wherein the adapter includes a step up transformer operable to convert the third electrosurgical waveform received by the return electrode to a fourth electrosurgical waveform.

2. The electrosurgical system according to claim 1, wherein the first electrosurgical waveform has a higher voltage level than the second electrosurgical waveform.

3. The electrosurgical system according to claim 1, wherein the first electrosurgical waveform has a lower current level than the second electrosurgical waveform.

4. The electrosurgical system according to claim 1, wherein the fourth electrosurgical waveform has a higher voltage level than the third electrosurgical waveform.

5. The electrosurgical system according to claim 1, wherein the fourth electrosurgical waveform has a lower current level than the third electrosurgical waveform.

6. An adapter suitable to connect a radio frequency ablation probe and return electrode to an electrosurgical generator, the adapter comprising:
a first transformer configured to receive a first electrosurgical waveform from the electrosurgical generator and convert the first electrosurgical waveform to a second electrosurgical waveform that is delivered to the radio frequency ablation probe; and
a second transformer configured to convert a third electrosurgical waveform from the return electrode to a fourth electrosurgical waveform that is delivered to the electrosurgical generator.

7. The adapter according to claim 6, wherein the first electrosurgical waveform has a higher voltage level than the second electrosurgical waveform.

8. The adapter according to claim 6, wherein the first electrosurgical waveform has a lower current level than the second electrosurgical waveform.

9. The adapter according to claim 6, wherein the fourth electrosurgical waveform has a higher voltage level than the third electrosurgical waveform.

10. The adapter according to claim 6, wherein the fourth electrosurgical waveform has a lower current level than the third electrosurgical waveform.

11. The adapter according to claim 6, further comprising a sensor module configured to detect at least one parameter of the first electrosurgical waveform, the second electrosurgical waveform, the third electrosurgical waveform or the fourth electrosurgical waveform.

12. The adapter according to claim 11, wherein the parameter is a voltage magnitude and/or phase or current magnitude and/or phase.

13. The adapter according to claim 10, further comprising a controller operable to control the first transformer or the second transformer.

* * * * *